United States Patent [19]

Ju

[11] Patent Number: 5,814,454
[45] Date of Patent: Sep. 29, 1998

[54] SETS OF LABELED ENERGY TRANSFER FLUORESCENT PRIMERS AND THEIR USE IN MULTI COMPONENT ANALYSIS

[75] Inventor: Jingyue Ju, Redwood City, Calif.

[73] Assignee: Incyte Pharmaceuticals, Inc., Palo Alto, Calif.

[21] Appl. No.: 968,327

[22] Filed: Nov. 12, 1997

Related U.S. Application Data

[62] Division of Ser. No. 784,162, Jan. 15, 1997.

[51] Int. Cl.$^6$ .............................. C12Q 1/68; C12P 19/34
[52] U.S. Cl. ............................................. 435/6; 435/91.2
[58] Field of Search ........................................ 435/6, 91.2

[56] References Cited

PUBLICATIONS

Ansorge, W., (1987) Automated DNA Sequencing: ultrasensitive detection of fluorescent bands during electrophoresis, *Nucl. Acids Res.* 15(11):4593–4602.

Glazer, A., et al., (1983) "Fluorescent Tandem Phycobiliprotein Conjugates," *Biophys. J.* 43:383–386.

Grifin, H., et al., (1993) "DNA Sequencing—Recent Innovations and Future Trends," *Appl. Biochem and Biotech.* 38: 147–159.

Huang, X. et al., (1992) "DNA Sequencing Using Capillary Array Electrophoresis," Anal. Chem. 64:2149–2154.

Ju, J., et al., (1995) "Design and Synthesis of Fluorescence Energy Transfer Dye–Labeled Primers and Their Application for DNA Sequencing and Analysis," *Anal. Bio.* 231: 131–140.

Ju, J., et al., (1995) "Fluorescence energy transfer dye–labeled primers for DNA sequencing and analysis," *Proc. Natl. Acad. Sci. USA* 92: 4347–4351.

Ju, J., et al., (1996) "Energy transfer primers: A new fluorescence labeling paradigm for DNA sequencing and analysis," *Nature Medicine* 2(2): 246–249.

Lu, H., et al., (1994) "High–speed and high–accuracy DNA sequencing by capillary gel electrophoresis in a simple, low cost instrument Two–color peak–height encoded sequencing at 40° C.," *J. Chromatography A* 680:497–501.

Matteucci, M., et al., (1996) "In pursuit of antisense," *Nature* 384: 20–22.

Prober, J., et al., (1987) "A System for Rapid DNA Sequencing with Fluorescent Chain–Terminating Dideoxynucleotides," *Science* 238:336–341.

Repp, R., et al., (1995) "Detection of Four Different 11q23 Chromosomal Abnormalities by Multiplex–PCR and Fluorescence–Based Automatic DNA–Fragment Analysis," *Leukemia* 1 9: 210–215.

Schena, M., et al., (1995) "Quantitative Monitoring of Gene Expression Patterns with a Complementary DNA Microarray," *Science* 270: 467–469.

Smith, L., et al., (1986) "Fluorescence detection in automated DNA sequence analysis," *Nature* 321:674–679.

Wang, Y., et al., (1995) "Rapid Sizing of Short Tandem Repeat Alleles Using Capillary Array Electrophoresis and Energy–Transfer Fluorescent Primers," *Anal. Chem.* 67(7): 1197–1203.

Ziegle, J., et al., (1992) "Application of Automated DNA Sizing Technology for Genotyping Microsatellite Loci," *Genomics,* 14: 1206–1031.

Rye, et al., Ti Nucleic Acis Res. tl (1991) vol. 19:327–331.

Primary Examiner—Eggerton A. Campbell
Attorney, Agent, or Firm—Bozicevic & Reed LLP; Bret E. Field

[57] ABSTRACT

Sets of fluorescent energy transfer labels and methods for their use in multi component analysis, particularly nucleic acid enzymatic sequencing, are provided. In the subject sets, at least two of the labels are energy transfer labels comprising a common donor and acceptor fluorophore in energy transfer relationship separated by different distances and capable of providing distinguishable fluorescence emission patterns upon excitation at a common wavelength. The subject labels find particular use in a variety of multi-component analysis applications, such as probes in FISH and multi array analyses, as well as primers in nucleic acid enzymatic sequencing applications.

10 Claims, 7 Drawing Sheets

SETS OF LABELED ENERGY TRANSFER FLUORESCENT PRIMERS AND THEIR USE IN MULTI COMPONENT ANALYSIS

This application is a divisional of U.S. patent application Ser. No. 08/784,162, filed Jan. 15, 1997, now, pending.

TECHNICAL FIELD

The field of this invention is fluorescent labels, particularly fluorescently labeled primers for use in DNA sequencing applications.

BACKGROUND OF THE INVENTION

Fluorescent labels find use in variety of different biological, chemical, medical and biotechnological applications. One example of where such labels find use is in polynucleotide sequencing, particularly in automated DNA sequencing, which is becoming of critical importance to large scale DNA sequencing projects, such as the Human Genome Project.

In methods of automated DNA sequencing, differently sized fluorescently labeled DNA fragments which terminate at each base in the sequence are enzymatically produced using the DNA to be sequenced as a template. Each group of fragments corresponding to termination at one of the four labeled bases are labeled with the same label. Thus, those fragments terminating in A are labeled with a first label, while those terminating in G, C and T are labeled with second, third and fourth labels respectively. The labeled fragments are then separated by size in an electrophoretic medium and an electropherogram is generated, from which the DNA sequence is determined.

As methods of automated DNA sequencing have become more advanced, of increasing interest is the use of sets of fluorescent labels in which all of the labels are excited at a common wavelength and yet emit one of four different detectable signals, one for each of the four different bases. Such labels provide for a number of advantages, including high fluorescence signals and the ability to electrophoretically separate all of the labeled fragments in a single lane of an electrophoretic medium which avoids problems associated with lane to lane mobility variation.

Although such sets of labels have been developed for use in automated DNA sequencing applications, heretofore the differently labeled members of such sets have each emitted at a different wavelength. Thus, conventional automated detection devices currently employed in methods in which all of the enzymatically produced fragments or primer extension products are separated in the same lane must be able to detect emitted fluorescent light at four different wavelengths. This requirement can prove to be an undesirable limitation. More specifically, carrying out sequencing on vast numbers of different DNA templates simultaneously increases the number of different fragments and corresponding labels required. At the same time, there is a need for a reduction in the complexity of the detection device, e.g. a device which can operate with light detection at only two wavelengths is preferable.

It would therefore be desirable to develop sets of fluorescent labels capable of providing four distinguishable signals, where the number of wavelengths associated with the four different signals is less than the number of different labels, e.g. where four different labels provide signals comprising emitted light at from one to two wavelengths. With such sets one could either: (1) reduce the complexity of automated detector devices or (2) increase the throughput of detectors capable of detecting at four different wavelengths, thereby achieving sequencing two DNA templates, or the same double stranded templates from both the 5' and 3' end, simultaneously.

RELEVANT LITERATURE

DNA sequencing is reviewed in Griffin & Griffin, Appl. Biochem. Biotechnol. (1993) 38:147–159. Fluorescence energy transfer labels and their use in DNA sequencing applications are described in Ju et al., Nucleic Acids Res. (1996) 24:1144–1148; Ju et al., Nat. Med. (1996) 2: 246–249; Ju et al., Anal. Biochem. (1995) 231: 131–140; Ju et al., Proc. Natl. Acad. Sci. U.S.A. (1995) 92: 4347–4351. Use of fluorescent energy transfer labels for non-DNA sequencing multi component analysis application is described in Wang et al., Anal. Chem. (1995) 67:1197–1203; Ziegle et al., Genomics (1992) 14: 1026–1031; and Repp et al., Leukemia (1995) 9: 210–215. Other references describing multi-component analysis applications include Schena et al., Science (1995) 270:467–469.

Other references of interest include U.S. Pat. Nos. 4,996,143 and 5,326,692, as well as Glazer and Streyer, Biophys. J. (1983) 43: 383–386, Huang et al., Anal. Chem. (1992) 64:2149–2154; Prober et al., Science (1987) 336–341; Smith et al., Nature (1986) 321: 674–679, Lu et al, J. Chromat. A (1994) 680: 497–501 and Ansorge et al., Nucleic Acids Res. (1987) 15: 4593–4603.

SUMMARY OF THE INVENTION

Sets of fluorescent labels, particularly labeled primers, as well as methods for their use in multi component analysis, are provided. At least two of the labels of the subject sets comprise a common donor and acceptor fluorescer component in energy transfer relationship separated by different distances, such that the labels provide distinguishable fluorescent signals upon excitation at a common light wavelength. The subject sets of labels find use in a variety of applications requiring a plurality of distinguishable fluorescent labels, and find particular use as primers in nucleic acid enzymatic sequencing applications. Primers with the same labels which produce distinguishable emission patterns can be produced because energy transfer between the acceptor and donor fluorphores is a function of the separation distance between the acceptor and donor in the label. By changing the distance, different fluorescence emission patterns are obtained.

DEFINITIONS

The term "fluorescent label" refers to a compound comprising at least one fluorophore bonded to a polymer.

The term "energy transfer fluorescent label" refers to a compound comprising at least two fluorophores in energy transfer relationship, where the fluorophores are bonded to a spacer component, e.g. a polymeric moiety, which separates the two fluorphores by a certain distance.

Figure 7:
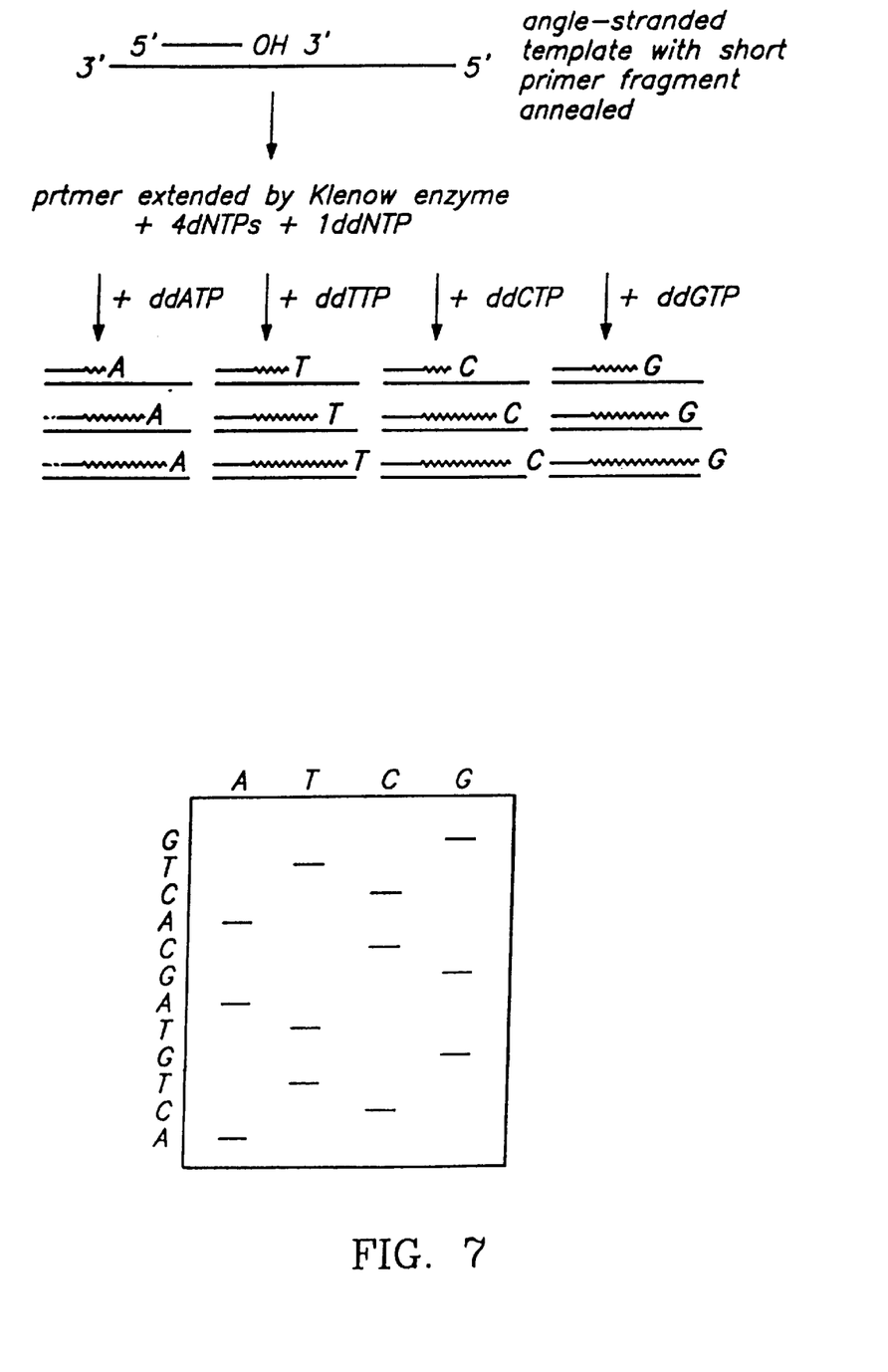
FIG. 7 is a shematic of the Sanger enzymatic DNA sequencing method.

The term "enzymatic sequencing," "Sanger Method," "dideoxy technique," and "chain terminator technique," are used interchangeably herein to describe a method of sequencing DNA named after its main developer, F. Sanger. The technique uses a single-stranded DNA template, a short DNA primer and a polymerase enzyme to synthesize a complementary DNA strand. The primer is first annealed to the single-stranded template and the reaction mixture is then split into four aliquots and deoxynucleoside triphosphates (dNTPs) plus a dideoxynucleoside triphosphate (ddNTP) are added such that each tube has a different ddNTP. The polymerase will incorporate a ddNTP opposite its complementary base on the template but no further dNTPs can be added as the ddNTP lacks a 3' hydroxyl group. The ratio of ddNTP to dNTP is such that the polymerase will terminate the growing DNA chain at all positions at which the ddNTP can be inserted and so a nested set of fragments (i.e. primer extension products) is formed which all have one end, the primer, in common. The fragments are labeled so that when the four reaction mixtures are electrophoresed through a polyacrylamide gel, a gel band pattern or ladder is formed from which the DNA sequence can be read directly. The process is shown schematically in FIG. 7.

The term "enzymatically produced" means produced at least in part as a result of an action of an enzyme, e.g. fragments of nucleotides are produced when an enzyme catalyzes a reaction whereby a larger sequences is cleaved into two or more fragments.

The term "primer" shall mean a polymer sequence which is complementary and capable of hybridizing to some part of a single stranded nucleotide sequence being sequenced which primer is used to initiate DNA synthesis in vitro.

DESCRIPTION OF THE SPECIFIC EMBODIMENTS

Sets of fluorescent labels, particularly sets of fluorescently labeled primers, and methods for their use in multi component analysis applications, particularly nucleic acid enzymatic sequencing applications, are provided. At least two of the label members of the set are energy transfer labels having a common donor and acceptor fluorophore separated by sufficiently different distances so that the two labels provide distinguishable fluorescent signals upon excitation at a common wavelength. In further describing the subject invention, the subject sets will first be described in greater detail followed by a discussion of methods for their use in multi component analysis applications.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

The subject sets of fluorescent labels comprise a plurality of different types of labels, wherein each type of label in a given set is capable of producing a distinguishable fluorescent signal from that of the other types of labels in different sets. Labels in the different sets generate different signals, preferably, though not necessarily upon excitation at a common excitation wavelength. For DNA sequencing applications, the subject sets will comprise at least 2 different types of labels, and may comprise 8 or more different types of labels, where for many applications the number of different types of labels in the set will not exceed 6, and will usually not exceed four, where at least two of the different types of labels are energy transfer labels sharing a common donor and acceptor fluorescer, as described in greater detail below. For other applications, such as fluorescence in situ hybridization (FISH), substantially more than 8 labels are ideal so that multiple targets can be analyzed.

The distinguishable signals generated by the "at least two energy transfer labels" will at least comprise the intensity of emitted light at one to two wavelengths. Preferably, the distinguishable signals produced by the "at least two energy transfer labels" will comprise distinguishable fluorescence emission patterns, which patterns are generated by plotting the intensity of emitted light from differently sized fragments at two wavelengths with respect to time as differently labeled fragments move relative to a detector, which patterns are known in the art as electropherograms. For analyses not based on electrophoresis, such as micro-array chip based assays, different targets tagged with a specific label can be differentiated from each other by the unique fluorescence patterns. For example, in one type of label of a set the intensity of emitted light at a first wavelength may be twice that of the intensity of emitted light at a second wavelength and in the second label the magnitude of the intensities of light emitted at the two wavelengths may be reversed, or light may be emitted at only one intensity. The different patterns are generated by varying the distance between the donor and acceptor. These patterns emitted from each of these labels are thus distinguishable.

The subject sets will comprise a plurality of different types of fluorescent labels, where at least two of the labels and usually all of the labels are energy transfer labels which comprise at least one acceptor fluorophore and at least one donor fluorophore in energy transfer relationship, where such labels may have more complex configurations, such as multiple donors and/or multiple acceptors, e.g. donor 1, acceptor 1 and acceptor 2. Critical to the subject sets is that at least two of the labels of the sets have common donor and accceptor fluorophores, where the only difference between the labels is the distance between these common acceptor and donor fluorophores. Thus, for sets of labels in which each label comprises a single donor and a single acceptor, at least one of the energy transfer labels will have a donor fluorophore and acceptor fluorophore in energy transfer relationship separated by a distance x and at least one of the energy transfer labels will comprise the same donor and acceptor fluorophores in energy transfer relationship separated by a different distance y, where the distances x and y are sufficiently different to provide for distinguishable fluorescence emission patterns upon excitation at a common wavelength, as described above. In those sets comprising a third label having the same donor and acceptor fluorophores as the first and second label, the distance z between the donor and acceptor fluorophore will be sufficiently different from x and y to ensure that the third label is capable of providing a distinguishable fluorescence emission pattern from the first and second labels. Thus, in a particular set of labels, one may have a plurality of labels having the same donor and acceptor fluorophores, where the only difference among the labels is the distance between the donor and acceptor fluorophores. To ensure that different types of labels of a set having common donor and acceptor fluorophores yield distinguishable fluorescence emission patterns, the distances between the donor and acceptor fluorophores will differ by at least about 5%, usually by at least about 10% and more usually by at least about 20% and will generally range from about from about 4 to 200 Å, usually from about 12 to 100 Å and more usually from about 15 to 80 Å, where the minimums in such distances are determined based on currently available detection devices and may be reduced as detection technology becomes more sensitive, therefore more distinct labels can be generated.

In one preffered embodiment, at least a portion of, up to and including all of, the labels of the subject sets will comprise a donor and acceptor fluorescer component in energy transfer relationship and covalently bonded to a spacer component, i.e. energy transfer labels. Thus, one could have a set of a plurality of labels in which only two of the labels comprise the above mentioned donor and acceptor fluorescer components and the remainder of the labels comprise a single fluorescer component. Preferably, however, all of the labels will comprise a donor and acceptor fluorescer component. Generally, for one donor and one acceptor ET systems, if a set comprises n types of energy transfer labels, the number of different types of acceptor fluorophores present in the energy transfer labels of the set will not exceed n−1. Thus, if the number of different types of energy transfer labels in the set is four, the number of different acceptor fluorophores in the set will not exceed 3, and will usually not exceed 2.

In other preferred embodiments, additional combinations of labels are possible. Thus, in a set of labels, two of the labels could be energy transfer labels sharing common donor and acceptor fluorophores separated by different distances and the remaining labels could be additional energy transfer labels with different donor and/or acceptor fluorophores, non-energy transfer fluorescent labels, and the like.

In the energy transfer labels of the subject sets, the spacer component to which the fluorescer components are covalently bound will typically be a polymeric chain or other chemical moiety capable of acting as a spacer for the donor and acceptor fluorophore components, such as a rigid chemical moiety, such as chemicals with cyclic ring or chain structures which can separate the donor and acceptor and which also can be incorporated with an active group for attaching to the targets to be analyzed, where the spacer component will generally be a polymeric chain, where the fluorescer components are covalently bonded through linking groups to monomeric units of the chain, where these monomeric units of the chain are separated by a plurality of monomeric units sufficient so that energy transfer can occur from the donor to acceptor fluorescer components. The polymeric chains will generally be either polynucleotides, analogues or mimetics thereof; or peptides, peptide analogues or mimetics thereof, e.g. peptoids. For polynucleotides, polynucleotide analogues or mimetics thereof, the polymeric chain will generally comprise sugar moieties which may or may not be covalently bonded to a heterocyclic nitrogenous base, e.g. adenine, guanine, cytosine, thymine, uracil etc., and are linked by a linking group. The sugar moieties will generally be five membered rings. e.g. ribose, or six membered rings, e.g. hexose, with five membered rings such as ribose being preferred. A number of different sugar linking groups may be employed, where illustrative linking groups include phosphodiester, phosphorothioate, methylene(methyl imino)(MMI), methophosphonate, phosphoramadite, guanidine, and the like. See Matteucci & Wagner, Nature (1996) Supp 84: 20–22. Peptide, peptide analogues and mimetics thereof suitable for use as the polymeric spacer include peptoids as described in WO 91/19735, the disclosure of which is herein incorporated by reference, where the individual monomeric units which are joined through amide bonds may or may not be bonded to a heterocyclic nitrogenous base, e.g, peptide nucleic acids. See Matteucci & Wagner supra. Generally, the polymeric spacer components of the subject labels will be peptide nucleic acid, polysugarphosphate as found in energy transfer cassettes as described in PCT/US96/13134, the disclosure of which is herein incorporated by reference, and polynucleotides as described in PCT/US95/01205, the disclosure of which is herein incorporated by reference.

Both the donor and acceptor fluorescer components of the subject labels will be covalently bonded to the spacer component, e.g. the polymeric spacer chain, through a linking group. The linking group can be varied widely and is not critical to this invention. The linking groups may be aliphatic, alicyclic, aromatic or heterocyclic, or combinations thereof. Functionalities or heteroatoms which may be present in the linking group include oxygen, nitrogen, sulfur, or the like, where the heteroatom functionality which may be present is oxy; oxo, thio, thiono, amino, amido and the like. Any of a variety of the linking groups may be employed which do not interfere with the energy transfer and gel electrophoresis, which may include purines or pyrimidines, particularly uridine, thymidine, cytosine, where substitution will be at an annular member, particularly carbon, or a side chain, e.g. methyl in thymidine. The donor and/or fluorescer component may be bonded directly to a base or through a linking group of from 1 to 6, more usually from 1 to 3 atoms, particularly carbon atoms. The linking group may be saturated or unsaturated, usually having not more than about one site of aliphatic unsaturation.

Though not absolutely necessarily, generally for DNA sequencing applications at least one of the donor and acceptor fluorescer components will be linked to a terminus of the polymeric spacer chain, where usually the donor fluorescer component will be bonded to the terminus of the chain, and the acceptor fluorescer component bonded to a monomeric unit internal to the chain. For labels comprising polynucleotides, analogues or mimetics thereof as the polymeric chain, the donor fluorescer component will generally be at the 5' terminus of the polymeric chain and the acceptor fluorescer component will be bonded to the polymeric chain at a position 3' position to the 5' terminus of the chain. For other applications, such as FISH, a variety of labeling approaches are possible.

The donor fluorescer components will generally be compounds which absorb in the range of about 300 to 900 nm, usually in the range of about 350 to 800 nm, and are capable of transferring energy to the acceptor fluorescer component. The donor component will have a strong molar absorbance co-efficient at the desired excitation wavelength, desirably greater than about $10^4$, preferably greater than about $10^5$ cm$^{-1}$M$^{-1}$. The molecular weight of the donor component will usually be less than about 2.0 kD, more usually less than about 1.5 kD. A variety of compounds may be employed as donor fluorescer components, including fluorescein, phycoerythrin, BODIPY, DAPI, Indo-1, coumarin, dansyl, cyanine dyes, and the like. Specific donor compounds of interest include fluoroscein, rhodamine, cyanine dyes and the like.

Although the donor and acceptor fluorescer component may be the same, e.g. both may be FAM, where they are different the acceptor fluorescer moiety will generally absorb light at a wavelength which is usually at least 10 nm higher, more usually at least 20 nm or higher, than the maximum absorbance wavelength of the donor, and will have a fluorescence emission maximum at a wavelength ranging from about 400 to 900 nm. As with the donor component, the acceptor fluorescer component will have a molecular weight of less than about 2.0 kD, usually less than about 1.5 kD. Acceptor fluorescer moieties may be rhodamines, fluoroscein derivatives, BODIPY and cyanine dyes and the like. Specific acceptor fluorescer moieties include FAM, JOE, TAM, ROX, BODIPY and cyanine dyes.

The distance between the donor and acceptor fluorescer components will be chosen to provide for energy transfer from the donor to acceptor fluorescer, where the efficiency of energy transfer will be from 20 to 100%. Depending on the donor and acceptor fluorescer components, the distance between the two will generally range from 4 to 200 Å, usually from 12 to 100 Å and more usually from 15 to 80 Å, as described above.

For the most part the labels of the subject sets will be described by the following formula:

wherein:
D is the donor fluorescer component, which may consist of more than two different donors separated by a spacer;
N is the spacer component, which may be a polymeric chain or rigid chemical moiety, where when N is a polymeric spacer that comprises nucleotides, analogues or mimetics thereof, the number of monomeric units in N will generally range from about 1 to 50, usually from about 4 to 20 and more usually from about 4 to 16;
A is the acceptor fluorescer component, which may consist of more than two different acceptors separated by a spacer; and
X is optional and is generally present when the labels are incorporated into oligonucleotide primers, where X is a functionality, e.g. an activated phosphate group, for linking to a mono- or polynucleotide, analogue or mimetic thereof, particularly a deoxyribonucleotide, generally of from 1 to 50, more usually from 1 to 25 nucleotides.

For sets to be employed in nucleic acid enzymatic sequencing in which the labels are to be employed as primers, the labels of the subject sets will comprise either the donor and acceptor fluorescer components attached directly to a hybridizing polymeric backbone, e.g. a polynucleotide, peptide nucleic acid and the like, or the donor and acceptor fluorescer components will be present in an energy transfer cassette attached to a hybridizable component where the energy transfer cassette comprises the fluorescer components attached to a non-hybridizing polymeric backbone, e.g. a universal spacer. See PCT/US96/13134 and Ju et al., Nat. Med. (1996) supra, the disclosures of which are herein incorporated by reference. The hybridizable component will typically comprise from about 8 to 40, more usually from about 8 to 25 nucleotides, where the hybridizable component will generally be complementary to various commercially available vector sequences such that during use, synthesis proceeds from the vector into the cloned sequence. The vectors may include single-stranded filamentous bacteriophage vectors, the bacteriophage lambda vector, pUC vectors, pGEM vectors, or the like. Conveniently, the primer may be derived from a universal primer, such as pUC/M13, λgt10, λgt11, and the like, (See Sambrook et al., Molecular Cloning: A Laboratory Manual, 2nd ed., CSHL, 1989, Section 13), where the universal primer will have been modified as described above, e.g. by either directly attaching the donor and acceptor fluorescer components to bases of the primer or by attaching an energy transfer cassette comprising the fluorescer components to the primer.

Sets of preferred energy transfer labels comprising donor and acceptor fluorescers covalently attached to a polynucleotide backbone in the above D-N-A format include: (1) F6R, F13R, F16R and F16F; where different formats can employed as long as the four primers display distinct fluorescence emission patterns.

The fluorescent labels of the subject sets can be readily synthesized according to known methods, where the subject labels will generally be synthesized by oligomerizing monomeric units of the polymeric chain of the label, where certain of the monomeric units will be covalently attached to a fluorescer component.

The subject sets of fluorescent labels find use in applications where at least two components of a sample or mixture of components are to be distinguishably detected. In such applications, the set will be combined with the sample comprising the to be detected components under conditions in which at least two of the components of the sample if present at all will be labeled with first and second labels of the set, where the first and second labels of the set comprise the same donor and acceptor fluorescer components which are separated by different distances. Thus, a first component of the sample is labeled with a first label of the set comprising donor and acceptor fluorescer components separated by a first distance X. A second component of the sample is labeled with a second label comprising the same donor and fluorescer components separated by a second distance Y, where X and Y are as described above. The labeled first and second components, which may or may not have been separated from the remaining components of the sample, are then irradiated by light at a wavelength capable of a being absorbed by the donor fluorescer components, generally at a wavelength which is maximally absorbed by the donor fluorescer components. Irradiation of the labeled components results in the generation of distinguishable fluorescence emission patterns from the labeled components, a first fluorescence emission pattern generated by the first label and second pattern being attributable to the second label. The distinguishable fluorescence emission patterns are then detected. Applications in which the subject labels find use include a variety of multicomponent analysis applications in which fluorescent labels are employed, including FISH, micro-array chip based assays where the labels may be used as probes which specifically bind to target components, DNA sequencing where the labels may be present as primers, and the like.

The subject sets of labels find particular use in polynucleotide enzymatic sequencing applications, where four different sets of differently sized polynucleotide fragments terminating at a different base are generated (with the members of each set terminating at the same base) and one wishes to distinguish the sets of fragments from each other. In such applications, the sets will generally comprise four different labels which are capable of acting as primers for enzymatic extension, where at least two of the labels will be energy transfer labels comprising differently spaced common donor and acceptor fluorescer components that are capable of generating distinguishable fluorescence emission patterns upon excitation at a common wavelength of light. Using methods known in the art, a first set of primer extension products all ending in A will be generated by using a first of the labels of the set as a primer. Second, third and fourth sets of primer extension products terminating in G, C and T will be also be enzymatically produced. The four different sets of primer extension products will then be combined and size separated, usually in an electrophoretic medium. The separated fragments will then be moved relative to a detector (where usually either the fragments or the detector will be stationary). The intensity of emitted light from each labeled fragment as it passes relative to the detector will be plotted as a function of time, i.e. an electropherogram will be produced. Since, the labels of the subject sets will generally emit light in only two wavelengths, the plotted electropherogram will comprise light emitted in two wavelengths. Each peak in the electropherogram will correspond to a particular type of primer extension product (i.e. A, G, C or T), where each peak will comprise one of four different fluorescence emission patterns. To determine the DNA sequence, the electropherogram will be read, with each different fluorescence emission pattern related to one of the four different bases in the DNA chain.

Where desired, two sets of labels according to the subject invention may be employed, where the distinguishable fluorescence emission patterns produced by the labels in the first set will comprise emissions at a first and second wavelength and the patterns produced by the second set of labels will comprise emissions at a third and fourth wavelength. By using two such sets in conjunction with one another, one could detect primer extension products produced from two different template DNA strands at essentially the same time in a conventional four color detector, thereby doubling the throughput of the detector.

The subject sets of labels may be sold in kits, where the kits may or may not comprise additional reagents or components necessary for the particular application in which the label set is to be employed. Thus, for sequencing applications, the subject sets may be sold in a kit which further comprises one or more of the additional requisite sequencing reagents, such as polymerase, nucleotides, dideoxynucleotides and the like.

The following examples are offered by way of illustration and not by way of limitation. The following examples are put forth so as to provide those of ordinary skill in the art with a complete disclosure and description of how to make and use the subject sets of fluorescent labels.

EXPERIMENTAL

A. Design and synthesis of the fluorescent primers.

Figure 1:
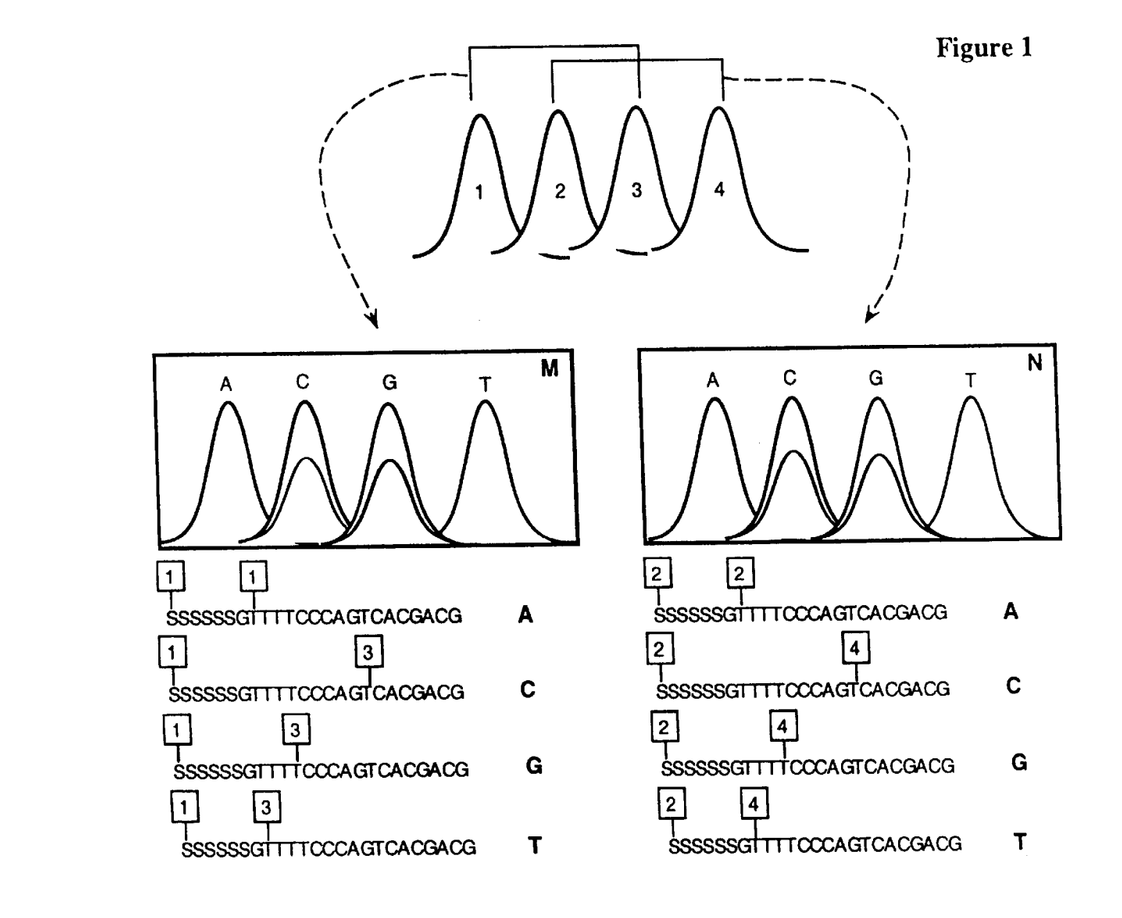
FIG. 1 shows the general labeling concept using four fluorescent molecules to generate at least eight fluorescent dye-labeled primers with distinguishable fluorescence emission patterns.
Figure 2:
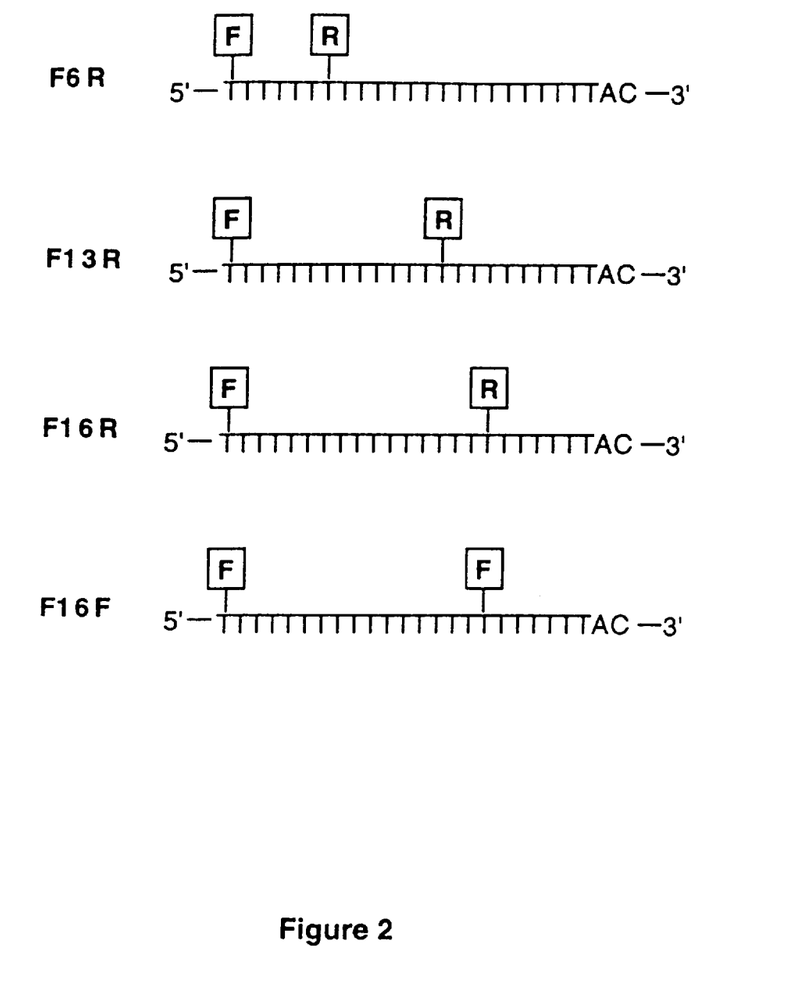
FIG. 2 shows the structure of the four primers labeled with two different fluorescent dyes, 6-carboxyfluoroscein (FAM, F) as a donor and 6-carboxyrhodamine (ROX, R) as an acceptor. The numbers in the primer name indicate the intervening nucleotides between the donor and acceptor.

An example of a general labeling scheme using the energy transfer concept to generate at least eight fluorescent primers from four fluorescent dyes is described in FIG. 1. To demonstrate the practicality of the labeling approach, two fluorescent dyes 6-carboxyfluorescein (FAM, F $\lambda_{em(max)}$=525 nm) as a donor and 6-carboxy-X-rhodamine (ROX, R $\lambda_{em(max)}$=605 nm, red) as an acceptor are chosen to generate four fluorescent oligonucleotide primers, which are subsequently used for DNA sequencing on a cDNA clone. The structures of the fluorescent primers are presented in FIG. 2. Oligodeoxynucleotides (25-bases long) with the sequence 5'-TTTTTTTTTTTTTTTTTTTTTTAC-3' (SEQ ID NO:01)were synthesized with donor-acceptor fluorophore pairs separated by different distances. The 25-mer contains a modified base introduced by the use of 5'-dimethoxytrityl-5-[N-(trifluoroacetylaminohexyl)-3-acryli mido]-2'-deoxyuridine, 3'-[(2-cyano-ethyl)-(N,N-diisopropyl)]-phosphoramidite (Amino-Modifier C6 dT, Glen Research, Sterling, Va.) which has a protected primary amine linker arm. The donor dye was attached to the 5' end of the oligomer, and the acceptor dye was attached to the primary amine group on the modified base. The primers are synthesized and purified according to the published procedure (Ju, J., Ruan, C., Fuller, C. W. Glazer, A. N. and Mathies, R. A. (1995) Proc. Natl. Acad. Sci. U.S.A. 92, 4347–4351). The ET primers are named using the abbreviation D-N-A, where D is the donor, A is the acceptor, and N is the number of intervening nucleotides between D and A. In all the primers prepared, 6-carboxyfluorescein (FAM, F, with fluorescence emission maximum at 525 nm) is selected as a common donor, and 6-carboxy-X-rhodamine (ROX, R, with fluorescence emission maximum at 605 nm) is selected as an acceptor, except in one example where N,N,N',N'-tetramethyl-6-carboxyrhodamine (TAMRA, T, with fluorescence emission maximum at 580 nm) is chosen as an acceptor as shown in FIG. 3.

Figure 3:
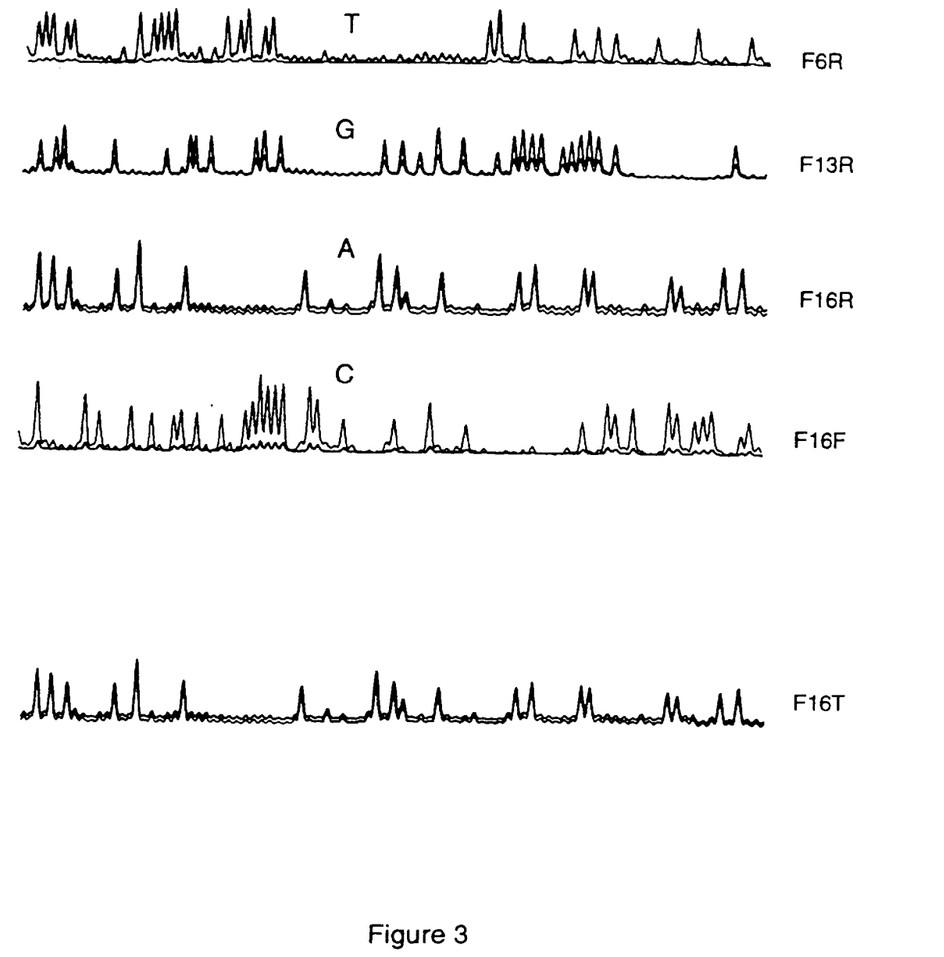
FIG. 3 shows that the fluorescence signal of the four fluorescent primers is sufficiently different to code for four nucleotides T (F6R), G (F13R), A (F16R), C (F16F). It also shows that the primer F16T using 6-carboxy tetramethyl rhodamine (TAMRA, T) to replace ROX (R) as an acceptor displays almost equal fluorescence signal intensity of F (blue) and T (black). The fluorescence signals shown are the electropherograms of the single base extension fragments from each primer obtained in the ABI four color fluorescent 377 DNA sequencer which has the appropriate filters to detect fluorescence signals from FAM (F $\lambda_{em(max)}$=605 nm), ROX (R $\lambda_{em(max)}$=605 nm) and TAMRA (T $\lambda_{em(max)}$=580 nm).

Five fluorescent primers with their unique fluorescence signal patterns are shown in FIG. 3. For primer F6R, the energy transfer efficiency from donor F to R is higher than 90%, therefore it only displays a dominant red color from acceptor R. For primer F13R, the ET efficiency is less than that in F6R, therefore F13R not only displays a high red signal from the acceptor R and also a blue signal from F with intensity approximately 40% of the red signal. For primer F16R, the ET efficiency is even less than that in F13R, which results in an approximately equal signal intensity from R (red) and F (blue). For primer F16F carrying two FAM molecules, the fluorescence signal is dominated by blue. For primer F16T that uses TAMRA (T) as an acceptor, the fluorescence signal from F (blue) is almost in equal intensity as T (Black). It is clear from these examples that at least five different fluorescent labels are generated using only three dyes. With two dyes FAM and ROX, four fluorescent primers are generated that have sufficiently different fluorescence signals to code for the for DNA sqeuencing fragments ended with nucleotides T (F6R), G (F13R, A (F16R) and C (F16F). These four primers are then chosen for evaluation in DNA sequencing using a cDNA clone with a polyA tail which can be primed by the designed primers.

B. DNA Sequencing procedure.

Sequencing was performed using a cDNA clone labeled Incyte clone 1 shown below and Thermo Sequenase sequencing kit (Amersham Life Science) on an ABI 377 sequencer.

INCYTE CLONE 1

Figure 6A:
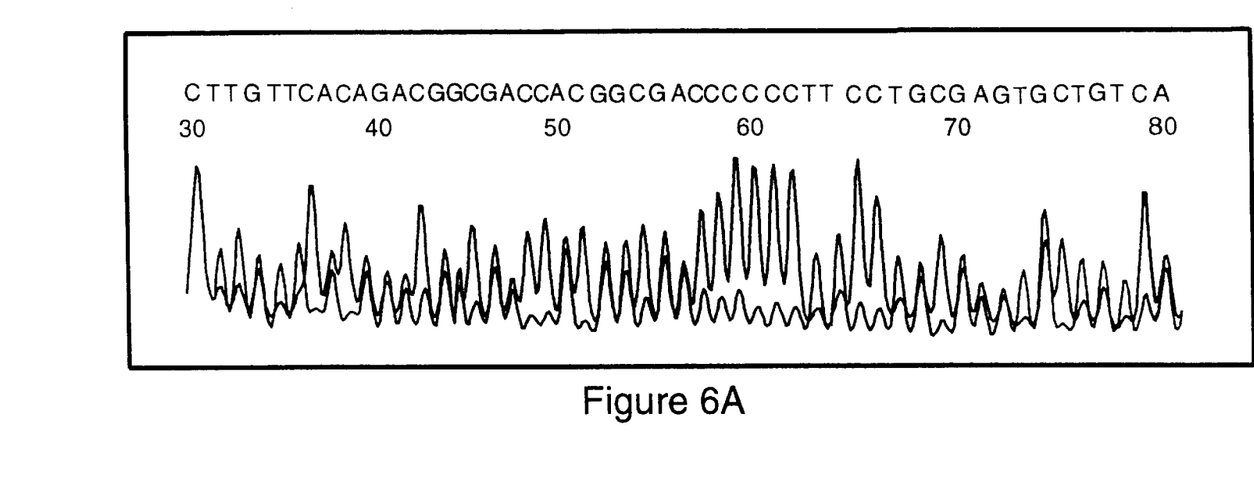
FIGS. 6A & 6B shows a large portion of the raw sequencing data (from nucleotide 30 to 130) in 2-color mode (FAM, F $\lambda_{em(max)}$=525 nm, blue; ROX, R $\lambda_{em(max)}$=605 nm, red) generated by primer F6R (T), F13R (G), F16R (A), F16F (C) and a cDNA clone which has a polyA tail at the 3' end. Sequences can be called by the color patterns of each peak. Samples were prepared using Thermo Sequenase Kit (Amersham LIFE SCIENCE) and run on a ABI 377 DNA sequencer with virtual filter A that detects the fluorescence signal from FAM and ROX.
Figure 6B:
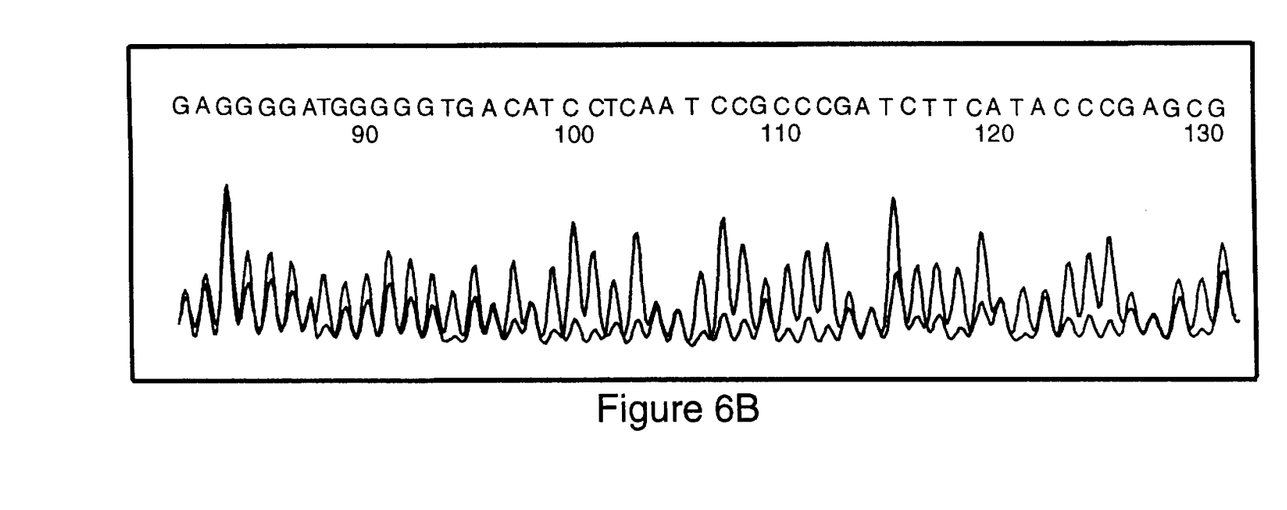

(The italic sequence is the one shown in FIG. 6.)

| CNCGNCCAGT | GAATTGTAAT | ACGACTCACT | ATAGGGCGAA | TTGGGTACCG |
|---|---|---|---|---|
| GGCCCCCCCT | CGAGTTTTTT | TTTTTTTTTT | TTTACATGAA | GGCAATTTAT |
| TAACAGAAAA | TATTTTGAGG | AATCTTGTTC | ACAGACGGCG | ACCACGGCGA |
| CCCCCCTTCC | TGCGAGTGCT | GTCAGAGGGG | ATGGGGGTGA | CATCCTCAAT |
| CCGCCCGATC | TTCATACCCG | AGCGGGCAAG | GGCTCTGAGG | GCCGACTGGG |
| CCCCAGGTCC | AGGGGTCTTG | GTCCTATTTC | CTCCTGTGGC | CCGGAGTTTG |
| (SEQ ID NO: 02) | | | | |

Four reactions were run, one for each dye/ddNTP combination with 0.2 pmole of the appropriate primer. The reactions containing ddCTP were run with the F16F primer, ddATP with the F16R primer, ddGTP with the F13R, and ddTTP with the F6R primer. Fifteen cycles of 94° C. for 20 seconds, 47° C. for 40 seconds and 68° C. for 60 seconds were carried out for the sequencing reaction mixture and then cooled to 4° C. The four reaction mixtures for each sequence were then combined into one vial and 50 μl of 100% ethanol were added to precipitate the DNA fragments. The DNA was precipitated by centrifugation for 30 min at 4° C. and then washed once with 70% ethanol. The precipitated DNA was vacuum dried, and resuspended in 4 μl of deionized formamide containing 8.3 mM EDTA and heated at 95° C. for 2 min. The denatured DNA was loaded on a 4% polyacrylamide 7M urea denaturing gel mounted in the instrument. Electrophoresis was conducted for 3.5 hours using 1× Tris-borate-EDTA buffer.

C. DNA sequencing results with the four fluorescent primers.

Figure 4:
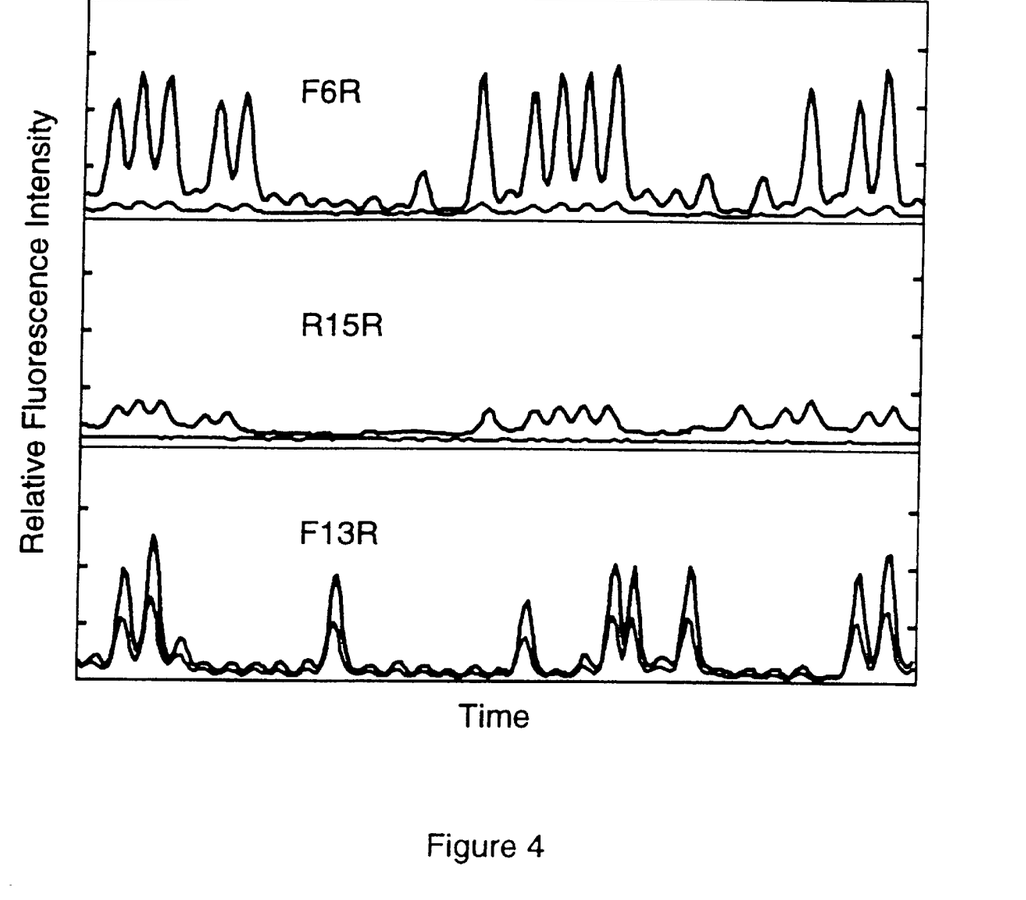
FIG. 4 shows that the fluorescence intensity of the single base extension fragments from primer F6R (T fragments) and F13R (G fragments) due to energy transfer from F to R is much higher than that of the single base fragments generated with primer R15R (T fragments) which carries two ROX dyes but with same sequence as F6R and F13R. Same concentration of the primer and other sequencing reagents were used in the comparison.
Figure 5:
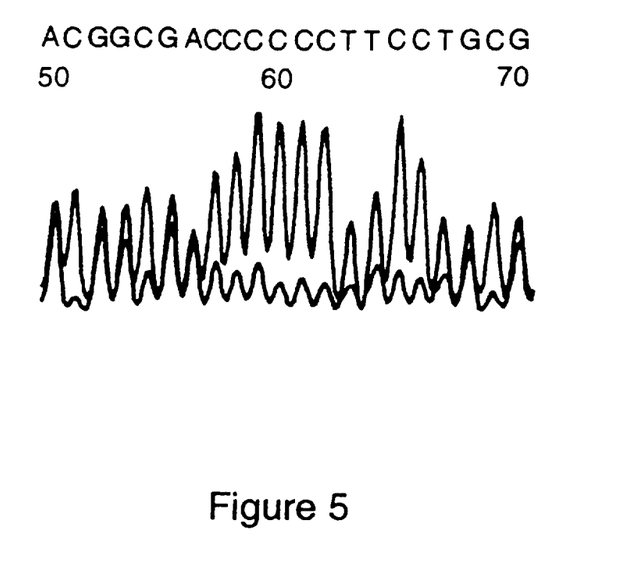
FIG. 5 shows a small portion of the raw sequencing data in 2-color mode (FAM, F $\lambda_{em(max)}$=525 nm, blue; ROX, R $\lambda_{em(max)}$=605 nm, red) generated by primer F6R (T), F13R (G), F16R (A), F16F (C) and a cDNA clone which has a polyA tail at the 3' end. Sequences can be called by the color patterns of each peak.

FIG. 4 shows that the fluorescence intensity of the single base extension fragments from primer F6R (T fragments) and F13R (G fragments) due to energy transfer from F to R is much higher than that of the single base fragments generated with primer R15R (T fragments) which carries two ROX dyes but with same sequence as F6R and F13R. The same concentration of the primer and other sequencing reagents were used in the comparison. A small portion of the DNA sequencing raw data in a two color mode sampled from FAM and ROX using primer F6R, F13R, F16R and F16F on an ABI 377 DNA sequencer is shown in FIG. 5. From this raw data, sequences can be determined by the color ratio of the peak in the electropherograms. FIG. 6 shows a large portion of the raw sequencing data (from nucleotide 30 to 130) in 2-color mode generated by primer F6R (T), F13R (G), F16R (A), F16F (C) and a cDNA clone which has a polyA tail at the 3' end. Sequences can be called by the color patterns of each peak without applying any mobility shift correction on the raw data. For example, when the blue and red signals under one peak have almost the same intensity, the peak is assigned as an A; when only a dominant blue signal is seen in a peak, it was assigned as a C; when red signal is slightly higher than the blue signal in a peak, it was assigned as a G; when the red signal is much higher than the blue signal in a peak, it was assigned as a T.

It is clear from the experimental data that with two fluorescent dyes, using energy transfer concepts which offer higher fluorescence signals, four fluorescent primers can be generated with sufficiently different fluorescence signal patterns for sequencing DNA successfully. With two additional different fluorescent molecules, using the same principle presented, another four fluorescent primers can be constructed. Thus, with a DNA sequencer equipped with the appropriate 4-color filters, two sets of DNA sequencing samples can be analyzed simultaneously, doubling the sequencing throughput. These sets of unique fluorescent labels constructed with the concepts presented will find wide applications in other multiple component analysis projects.

It is evident from the above results and discussion that the sets of a labels of the subject invention provide for a number of advantages. For example, where the sets of labels are employed in DNA sequencing, one can employ a detector capable of detecting at only two very well separated wavelengths. Therefore, the detector can sample a large portion of the fluorescence signals, providing higher sensitivity for detection and increasing readlength of the sequence. Alternatively, with conventional detectors comprising four different wavelength detectors, one can effectively double the throughput obtainable with these detectors by sequencing two different strands with two sets of labels according to the subject invention. Thus, the subject sets of labels represent a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of sequencing a DNA molecule, said method comprising:

enzymatically producing four sets of primer extension products using said DNA molecule as a template, wherein each of said sets comprises a family of different sized primer extension products terminating at the same base, and further wherein each of said sets comprises the same fluorescent label, wherein the fluorescent labels from at least two of said sets comprise the same donor and acceptor fluorophores in energy transfer relationship separated by different distances and capable of providing distinguishable fluorescence emission patterns, wherein all of the labels of said set are acceptor fluorophores selected from the group consisting of TAM, JOE, FAM, ROX, BODIPY, fluorescein and cyanine dyes;

size separating said primer extension products;

detecting said size separated primer extension products; and determining the sequence of said DNA molecule from said detected size separated primer extension products.

2. The method according to claim 1, wherein said detecting comprises irradiating said primer extension products at a common wavelength and distinguishing said distinguishable fluorescence emission patterns.

3. The method according to claim 2, wherein said method further comprises producing an electropherogram plotting the emission intensity at two wavelengths of each of said primer extension products as a function of time and said sequence is derived from said electropherogram.

4. A method of sequencing a DNA molecule, said method comprising:

enzymatically producing a first set of primer extension products terminating in A using a first energy transfer fluorescently labeled oligonucleotide primer comprising a donor fluorophore and an acceptor fluorophore in energy transfer relationship separated by a distance x;

enzymatically producing a second set of primer extension products terminating in G using a second energy transfer fluorescently labeled oligonucleotide primer comprising said donor fluorophore and said acceptor fluorophore in energy transfer relationship separated by a distance y, wherein all of the labels of said set are acceptor flourophores selected from the group consisting of TAM, JOE, FAM, ROX, BODIPY, fluorescein and cyanine dyes;

enzymatically producing a third set of primer extension products terminating in T using a third energy transfer fluorescently labeled oligonucleotide primer comprising said donor fluorophore and said acceptor fluorophore in energy transfer relationship separated by a distance z; and enzymatically producing a fourth set of primer extension products terminating in C using a fourth energy transfer fluorescently labeled oligonucleotide primer wherein said donor and acceptor fluorophore are the same;

wherein said first through fourth fluorescent labels are capable of providing distinguishable fluorescence emission patterns;

combining said four sets of primer extension products;

size separating said primer extension products;

irradiating said size separated primer extension products whereby each of said side separated product emits a distinguishable fluorescence emission pattern;

producing an electropherogram by plotting the intensity of emitted light at two wavelengths as a function of time as each primer extension product passes relative to a detector; and determining the sequence of said DNA molecule from said electropherogram.

5. A method of determining the presence of at least two different components in a sample, said method comprising:

labeling a first component of said sample with a first fluorescent label comprising at least one donor and at least one acceptor fluorescer component separated by a distance X;

labeling a second component of said sample with a second fluorescent label comprising said at least one donor and said at least one acceptor fluorescer components separated by a distance Y, wherein Y is different from X, wherein all of the labels of said set are acceptor fluorophores selected from the group consisting of TAM, JOE, FAM, ROX, BODIPY, fluoroscein and cyanine dyes;

irradiating said sample with light at a wavelength absorbed by said acceptor fluorescer component, whereby said first and second labels emit distinguishable fluorescence emission patterns;

detecting said distinguishable fluorescence emission patterns; and determining the presence of said two different components from said detection.

6. The method according to claim 5, wherein said first and second fluorescent labels are energy transfer labeled oligonucleotide primers and said first and second components are primer extension products comprising said primers.

7. The method according to claim 5, wherein said first and second fluorescent labels are energy transfer dye labeled probes and said first and second components are targets which specifically bind to said probes.

8. A kit for use in DNA sequencing, said kit comprising:

a set of four fluorescently labeled oligonucleotide primers, wherein at least two of said oligonucleotide primers have a common donor and acceptor fluorophore in energy transfer relationship and are separated by different distances, wherein all of the labels of said set are acceptor fluorophores selected from the group consisting of TAM, JOE, FAM, ROX, BODIPY, fluoroscein and cyanine dyes.

9. The kit according to claim 8, wherein said kit further comprises polymerase.

10. The kit according to claim 8, wherein said kit further comprises deoxynucleotides and dideoxynucleotides.

* * * * *